(12) United States Patent
Narita

(10) Patent No.: US 8,132,950 B2
(45) Date of Patent: Mar. 13, 2012

(54) LIGHT SOURCE DEVICE FOR ENDOSCOPE

(75) Inventor: Satoshi Narita, Saitama (JP)

(73) Assignee: Fujifilm Corporation, Tokyo (JP)

( * ) Notice: Subject to any disclaimer, the term of this patent is extended or adjusted under 35 U.S.C. 154(b) by 426 days.

(21) Appl. No.: 12/398,673

(22) Filed: Mar. 5, 2009

(65) Prior Publication Data

US 2009/0225548 A1    Sep. 10, 2009

(30) Foreign Application Priority Data

Mar. 6, 2008   (JP) ................................. 2008-056324

(51) Int. Cl.
   *A61B 1/06*   (2006.01)
(52) U.S. Cl. ........ 362/574; 362/253; 362/277; 362/572; 362/265; 362/321
(58) Field of Classification Search .................. 362/253, 362/277, 572, 574, 265, 321; 600/101, 160, 600/476

See application file for complete search history.

(56) References Cited

U.S. PATENT DOCUMENTS

2003/0191368 A1* 10/2003 Wang et al. .................... 600/160

FOREIGN PATENT DOCUMENTS

| JP | 8-15617 A | 1/1996 |
|---|---|---|
| JP | 2000-56240 A | 2/2000 |
| JP | 2000-189383 A | 7/2000 |
| JP | 2007-195850 A | 8/2007 |

* cited by examiner

*Primary Examiner* — Stephen F Husar
*Assistant Examiner* — Meghan Dunwiddie
(74) *Attorney, Agent, or Firm* — Birch, Stewart, Kolasch & Birch, LLP

(57) ABSTRACT

A light source device includes a xenon lamp, a rotary shutter, a main CPU for controlling drive of these components, and a sub CPU. The main CPU operates when receiving a reset cancel signal from a reset circuit. Between the sub CPU and the reset circuit, an AND circuit is provided. When the reset cancel signal from the reset circuit and a lighting completion signal indicating completion of lighting the xenon lamp are both input, the AND circuit outputs the reset cancel signal to the sub CPU. After the output of the lighting completion signal, the sub CPU operates to drive the rotary shutter. When high-frequency noise which occurs at the time of discharging the xenon lamp stops, the rotary shutter is activated and thereby generating pulses of illumination light.

5 Claims, 4 Drawing Sheets

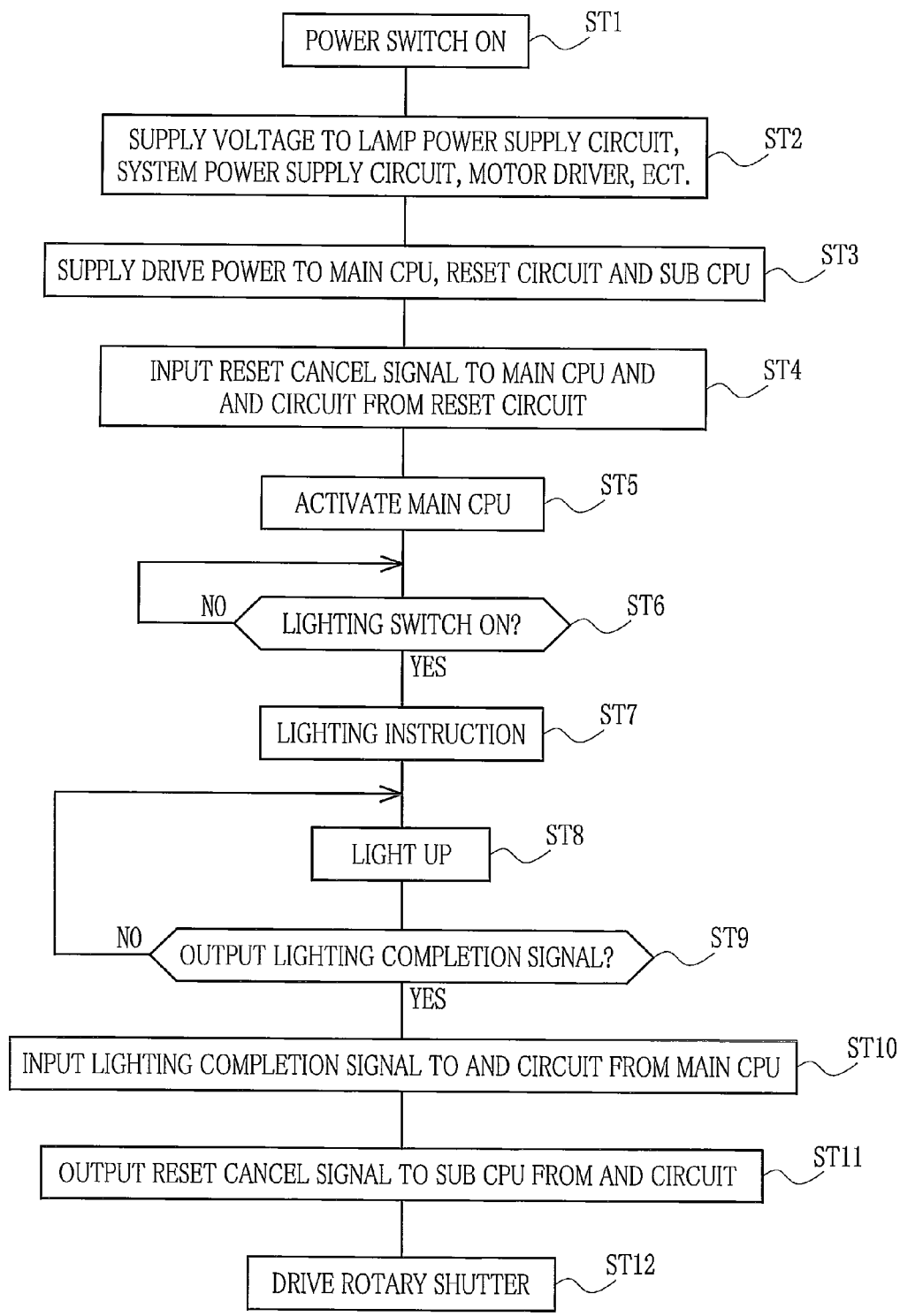

LIGHT SOURCE DEVICE FOR ENDOSCOPE

FIELD OF THE INVENTION

The present invention relates to a light source device that supplies an endoscope with illumination light for illuminating inside a human body cavity to inspect.

BACKGROUND OF THE INVENTION

A light source device for an endoscope emits illumination light from a light source, and the illumination light is supplied to the endoscope through a universal cord. In the endoscope, the illumination light is introduced, through a light guide, to a distal portion of an insert section, and thereby illuminating inside a human body cavity. When the illumination light is emitted for a long time, optical members and other components of the light source device may be heated up and damaged. In view of this, the light source device is provided with a light quantity controller for controlling the quantity of the illumination light. In the endoscope having an imaging sensor at the distal portion of the insert section, increase in a heating value may cause thermal noise to the imaging sensor, which may lower image quality or damage the material of the distal portion of the insert section. Therefore, such an endoscope especially needs to adjust the quantity or illumination periods of the illumination light. In addition, the light guide provided inside the endoscope is constituted of a bundle of optical fibers. The quantity of the illumination light guided to the distal portion of the insert section increases with increase in the number of the optical fibers. As a result, the heating value is raised and its effects become severe.

Such light source devices provided with the above-described light quantity controller are disclosed in, for example, Japanese Patent Application Laid-open Publications No. 8-15617 and No. 2000-56240. The light source devices disclosed in these publications include a light quantity detection circuit for detecting light quantity based on an imaging signal output from an imaging sensor of an endoscope and a controller for making a light source perform pulse-lighting such that the light source emits the illumination light in synchronization with exposure periods of the imaging sensor.

In addition, a light source device disclosed in Japanese Patent Application Laid-open Publication No. 2000-189383 is constituted of an endoscope having a light guide and an optical guide, and a TV camera connected to a rear end of the endoscope. Illumination light from the light guide illuminates a human body cavity. An image of the human body cavity is transmitted to the TV camera through the optical guide and is converted into an image signal by an imaging sensor inside the TV camera.

In Japanese Patent Application Laid-open Publication No. 2000-189383, the illumination light from a light source is transmitted through the light guide of the endoscope. The light source device is provided with an aperture adjustment mechanism for adjusting the illumination light from the light source and a judgment device for judging whether to control the illumination light based on variation in brightness distribution generated from a video signal output from the imaging sensor of the TV camera. When the judgment device judges as the control of the illumination light is needed, the aperture adjustment mechanism puts an aperture blade into a close position to block the illumination light.

In the light source device of Japanese Patent Application Laid-open Publication No. 2000-189383 provided with the aperture adjustment mechanism, the quantity of the illumination light for illuminating the human body cavity is reduced when the aperture is made small. As a result, the image becomes dark and cannot be observed well on a monitor. In view of this, an electronic endoscope disclosed in Japanese Patent Application Laid-open Publication No. 2007-195850 has a rotary shutter having a rotating light-blocking plate and a controller for controlling the rotary shutter, in addition to the light quantity controller like the aperture adjustment mechanism. For this configuration, illumination periods for illuminating a subject and light-blocking periods for blocking the illumination light are alternately repeated by rotating the rotary shutter. At this time, the rotary shutter is controlled such that the illumination periods are synchronized with the exposure periods of the imaging sensor. Owing to this, sufficient quantity of light for illuminating the subject can be obtained with simple configuration and the heating value can be lowered by controlling the illumination periods for illuminating the subject.

Meanwhile, as the light source for the light source device, a discharge lamp, such as a xenon lamp, featuring high brightness and long life is used instead of a halogen lamp in recent years. At the time of lighting up the xenon lamp, high voltage is applied to a xenon tube to start an electric discharge. After completing the light up, steady voltage which is lower than the voltage applied at the time of discharging is applied to keep illuminating the lamp.

In the light source devices disclosed in Japanese Patent Application Laid-open Publications No. 8-15617 and No. 2000-56240, the quantity of the illumination light is adjusted by performing the pulse-lighting of the light source. However, when the above-described xenon lamp is used as the light source, it is hard to control the illumination periods because the xenon lamp takes time to be lit up once it is turned off. In addition, the xenon lamp may consecutively generate the high-frequency noise each time the lamp is lit up in the pulse-lighting.

The rotary shutter like the one disclosed in Japanese Patent Application Laid-open Publication No. 2007-195850 is advantageous in view of cost and mechanical properties as compared to the pulse-lighting or the aperture adjustment mechanism. However, when the xenon lamp is used for the light source device having the rotary shutter, a driver circuit of the rotary shutter may have malfunction due to high-frequency noise which occurs at the time of starting the electric discharge of the xenon lamp. The malfunction may cause loss of synchronization of a motor of the rotary shutter. When the loss of synchronization occurs, the rotating light-blocking plate may stop at a position corresponding to the light-blocking period and the illumination light may be blocked even in the illumination period, and then the monitor screen may turn black.

SUMMARY OF THE INVENTION

An object of the present invention is to provide a light source device for an endoscope capable of preventing malfunction of a rotary shutter due to high-frequency noise which occurs at the time of starting an electric discharge of a discharge lamp.

In order to achieve the above and other objects, a light source device for an endoscope of the present invention includes a discharge lamp, a lamp controller, a rotary shutter, a drive controller, and an operation controller. The discharge lamp emits illumination light for illuminating inside a human body cavity. The lamp controller controls emission of the discharge lamp. The lamp controller also outputs a lighting completion signal at the time of completing light up of the discharge lamp. The rotary shutter opens and closes an optical axis of the illumination light, and thereby alternatively providing an illumination period for passing the illumination light and a light-blocking period for blocking the illumination light at a constant period. The drive controller controls rotation of the rotary shutter. The operation controller does not activate the drive controller before the lighting completion signal is output but activates the drive controller after the lighting completion signal is output.

The rotary shutter has a rotating plate in which a cutout corresponding to the illumination period is formed, and a motor for rotating the rotating plate.

The operation controller includes a rest circuit and an AND circuit. The reset circuit outputs a reset cancel/reset signal to the lamp controller and the drive controller according to a power on/off. The AND circuit is provided between the drive controller and the reset circuit and obtains AND of the lighting completion signal and the rest cancel/reset signal. The operation controller activates the drive controller when both of the reset signal and the lighting completion signal are input to the AND circuit.

The discharge lamp is preferably a xenon lamp. The lamp controller is preferably a main CPU for taking overall control of the light source device. The drive controller is preferably a sub CPU provided separately from the lamp controller.

According to the present invention, the operation controller does not activate the rotary shutter until the lighting completion signal is output. Owing to this, malfunction of the rotary shutter due to high-frequency noise which occurs at the time of starting the electric discharge of the discharge lamp can be prevented.

BRIEF DESCRIPTION OF THE DRAWINGS

One with ordinary skill in the art would easily understand the above-described objects and advantages of the present invention when the following detailed description is read with reference to the drawings attached hereto:

FIG. 4 is a flow chart showing procedures from turning on a power switch until a rotary shutter is driven.

DESCRIPTION OF THE PREFERRED EMBODIMENTS

Figure 1:
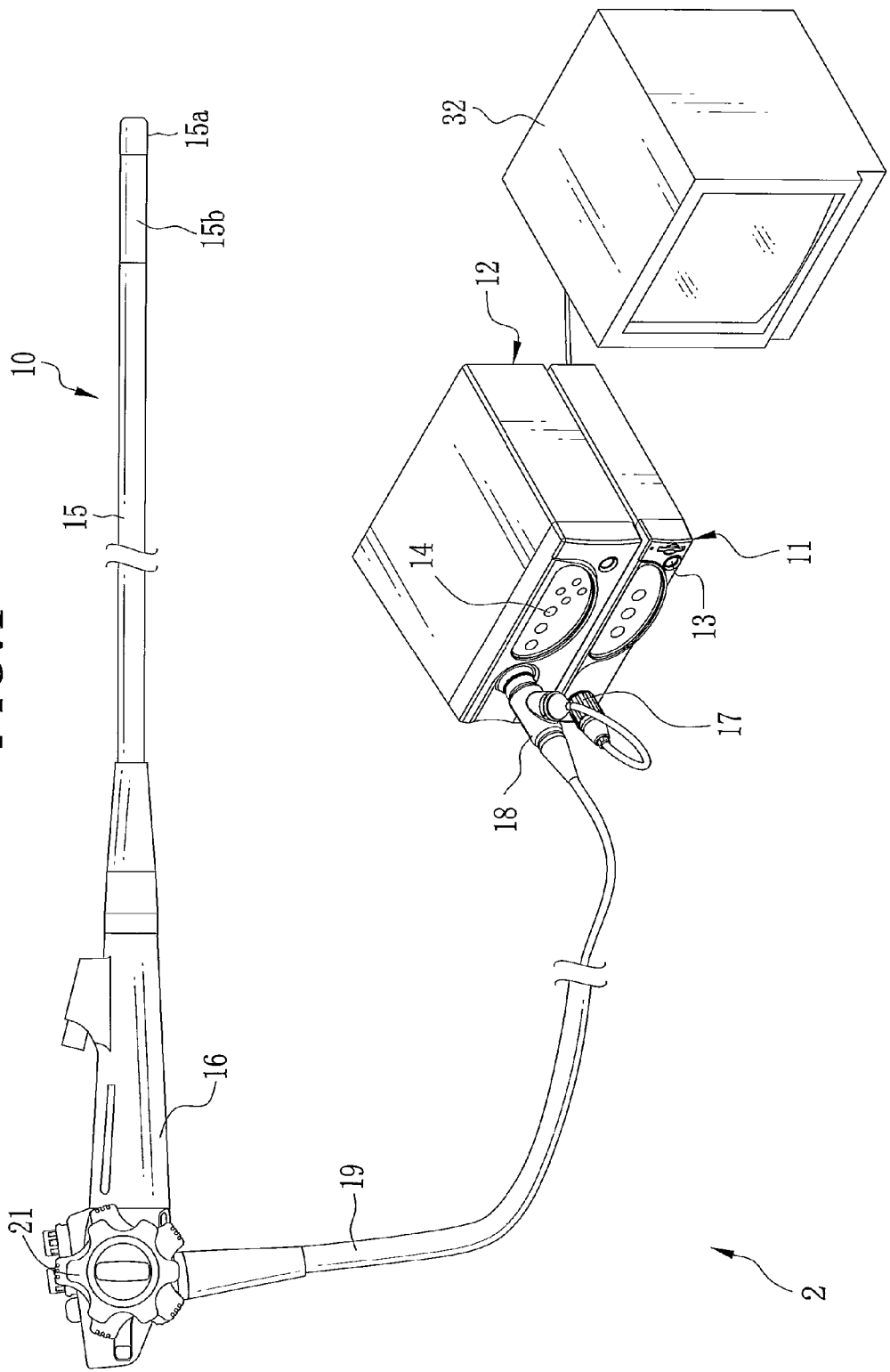
FIG. 1 is an external view illustrating an electronic endoscope system.

In FIG. 1, an electronic endoscope system 2 is constituted of an electronic endoscope 10, a processor 11 and a light source device 12. A power switch 13 for turning on/off the electronic endoscope system 12 is provided at a front surface of the processor 11. A lighting switch 14 for turning on/off a xenon lamp 33 (see FIG. 2) is provided at a front surface of the light source device 12. The electronic endoscope 10 is provided with a flexible insert section 15 that is introduced into a body cavity, a handling section 16 that is jointed to a base end of the insert section 15, a communication connector 17 that is connected to the processor 11, a light source connector 18 that is connected to the light source device 12, and a universal cord 19 connecting the handling section 16 and the connectors 17, 18. The processor 11 is electrically connected to the electronic endoscope 10 and the light source device 12, and takes overall control of the electronic endoscope system 2.

In a distal portion 15a of the insert section 15 contains a CCD image sensor (hereinafter referred to as CCD) 20 (see FIG. 2), which captures images inside the body cavity. Behind the distal portion 15a is mounted a bending portion 15b, which consists of serially linked ring-like segments. The bending portion 15b may curve in any directions to direct the distal portion 15a toward anywhere inside the body cavity. To curve the bending portion 15b, actuating an angle knob 21 on the handling section 16 pushes or pulls some wires that extend through the insert section 15.

Figure 2:
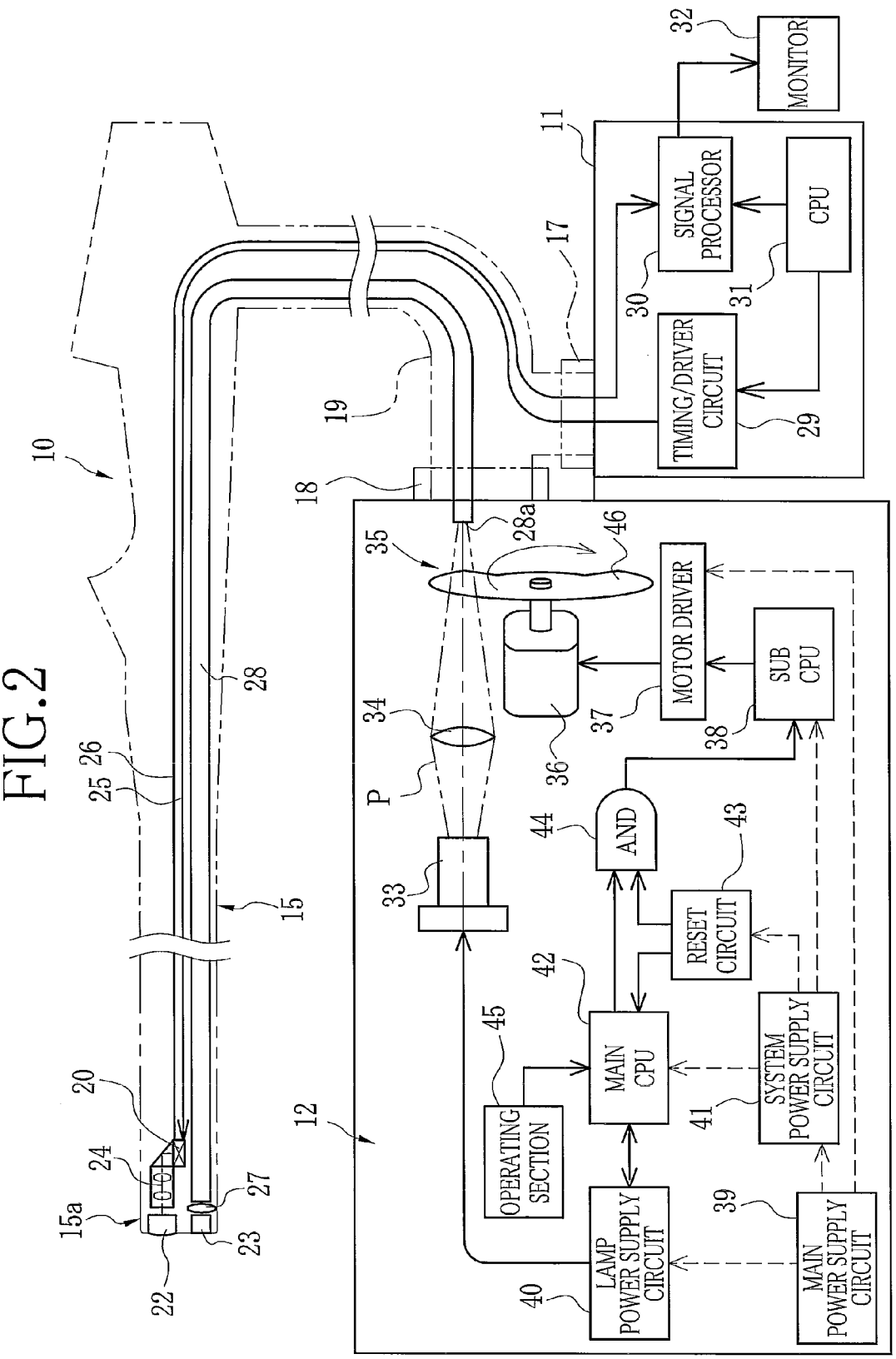
FIG. 2 is a block diagram schematically illustrating an electric structure of the electronic endoscope system.

FIG. 2 shows a face end of the distal portion 15a of the electronic endoscope 10, having an observation window 22 and a lighting window 23. Behind the observation window 22, an optical system 24 for taking an optical image of a target body part is mounted, and at the back of the optical system 24, the CCD 20 is located. The CCD 20 is, for example, an interline CCD. Inside of the universal cord 19 is provided signal lines 25, 26 that intermediate communication of various signals between the CCD 20 and the light source device 12. The signal lines 25, 26 are connected to the processor 11 through the communication connector 17. Instead of the CCD 20, a CMOS image sensor may also be used as the imaging sensor.

Meanwhile, behind the lighting window 23, a projection lens 27 is located. The projection lens 27 faces an exit end of the light guide 28. The light guide 28 goes through inside the insert section 15, the handling section 16, the universal cord 19 and the light source connector 18. An incident end 28a of the light guide 28 is exposed from a rear end of the light source connector 18. The light guide 28 consists of a number of optical fibers (made of for example quartz) tied into a bundle.

The processor 11 is provided with a timing/driver circuit 29, a signal processor 30, and a CPU 31 for controlling these parts. When the communication connector 17 of the electronic endoscope 10 is connected to the processor 11, the CCD 20 is connected to the timing/driving circuit 29 through the signal line 25 and to the signal processor 30 through the signal line 26. The timing/driving circuit 29 controls discharge timing of the electric charge of the CCD 20, a shutter speed of an electronic shutter of the CCD 20 (charge accumulation time), and the like on a timing signal (clock pulse) generated according to a command from the CPU 31. An imaging signal output from the CCD 20 is subjected to various image processing like amplification and A/D conversion in the signal processor 30 to be a video signal. The video signal is sent to a monitor 32 connected to the processor 11 via a cable (see FIG. 1) and displayed as an endoscopic image on a screen of the monitor 32.

The light source device 12 is provided with the xenon lamp 33 for emitting illumination light, a converging lens 34, a rotary shutter 35 having a rotating plate 46 and a motor 36, a motor driver 37, a sub CPU 38 for controlling the motor driver 37, a main power supply circuit 39, a lamp power supply circuit 40, a system power supply circuit 41, a main CPU 42 for taking overall control of the light source device 12, a reset circuit 43, an AND circuit 44, and an operating section 45 including the lighting switch 14. The light emitted from the xenon lamp 33 is converged by the converging lens 34 and guided to the incident end 28a of the light guide 28. Instead of the xenon lamp 33, another discharge lamp may also be used as the light source.

The main power supply circuit 39 feeds power supply voltage to the lamp power supply circuit 40 and the system power supply circuit 41, the motor driver 37, and the like upon turning on the power switch 13. The system power supply circuit 41 supplies drive power to the main CPU 42, the reset circuit 43, the sub CPU 38, and the like by transforming the power supply voltage. The reset circuit 43 outputs either a reset signal or a reset cancel signal. When operations of peripheral circuits are unstable, the reset circuit 43 keeps outputting the reset signal to the main CPU 42 and the AND circuit 44. When the drive power is normally supplied from the system power supply circuit 41 and once the operations of the peripheral circuits become stable, the reset circuit 43 outputs the reset cancel signal to the main CPU 42 and the AND circuit 44. Upon receipt of the reset cancel signal from the reset circuit 43 after receiving the drive power from the system power supply circuit 41, the main CPU 42 starts to operate. After the main CPU 42 starts operating, the lighting switch 14 is turned on. Then the main CPU 42 inputs a lighting instruction signal to the lamp power supply circuit 40.

The lamp power supply circuit 40 supplies drive power to the xenon lamp 33 by transforming the power supply voltage from the main power supply circuit 39. The lamp power supply circuit 40 firstly applies a trigger voltage (for example, 30 KV) to the xenon lamp 33 according to the lighting instruction signal input from the main CPU 42, and thereby starts lighting up by arc discharge. After starting the lighting, the lamp power supply circuit 40 applies a steady voltage (for example, 12 V) which is lower than the trigger voltage to apply electric current for illumination. When the electric current for illumination is stably applied for longer than a specific period of time, the lamp power supply circuit 40 outputs a lighting completion signal indicating stable illumination of the xenon lamp 33 to the main CPU 42. When the lighting completion signal is input from the lamp power supply circuit 40, the main CPU 42 outputs the lighting completion signal to the AND circuit 44. Note that the lighting completion signal output from the lamp power supply circuit 40 can directly be input to the AND circuit 44 without going through the main CPU 42.

An input terminal side of the AND circuit 44 is connected to the main CPU 42 and the reset circuit 43, whereas an output terminal side of the AND circuit 44 is connected to the sub CPU 38. The AND circuit 44 takes AND of the lighting completion signal from the main CPU 42 and the reset cancel/reset signal from the reset circuit 43, and determines an output according to a truth table shown in Table 1. When the power is off (reset cancel signal "0"), the xenon lamp 33 never light up (lighting completion signal never become "1"), and therefore such a case is not shown in Table 1.

TABLE 1

| Reset cancel signal | Lighting completion signal | AND circuit output | Status |
|---|---|---|---|
| 1 | 1 | 1 | power off/xenon lamp on (stable) |
| 1 | 0 | 0 | power on/xenon lamp off or start of discharge |
| 0 | 0 | 0 | power off |

According to Table 1, the AND circuit 44 outputs the reset cancel signal to the sub CPU 38 only when the reset cancel signal and the lighting completion signal are both input. After the drive power is being supplied, the sub CPU 38 is not actuated until the reset cancel signal is input from the AND circuit 44. Owing to this, the motor driver 37 is not activated, and therefore neither the motor 36 nor the rotating plate 46 is rotated. Once the reset cancel signal is input from the AND circuit 44, the sub CPU 38 starts operation and outputs a drive control signal to the motor driver 37 to activate it. When the drive control signal is input from the sub CPU 38, the motor driver 37 supplies a drive pulse to the motor 36, and thereby driving and rotating the rotating plate 46.

In this embodiment, the main CPU 42 which mainly controls the illumination of the xenon lamp 33 and the sub CPU 38 which controls the drive of the rotary shutter 35 are separately provided. For this configuration, even when the operation of one CPU falls unstable due to external disturbance like noise, it does not affect the operation of the other CPU, which enhances stability and resistance against the external disturbance. For example, when the operation of the main CPU 42 becomes unstable, the control of the xenon lamp 33 may be disturbed, but even in this case, the rotation of the rotary shutter 35 can be controlled as long as the sub CPU 38 functions normally. Note that the illumination of the xenon lamp 33 and the rotation of the rotary shutter 35 can be controlled by a single CPU.

Figure 3A:
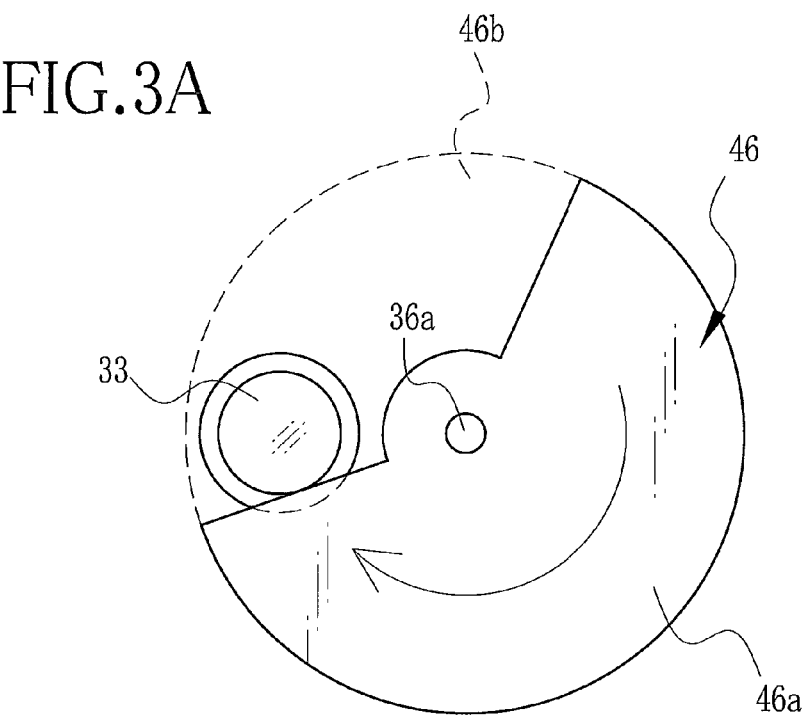
FIGS. 3A and 3B are plane views respectively illustrating a rotating plate of a rotary shutter.
Figure 3B:
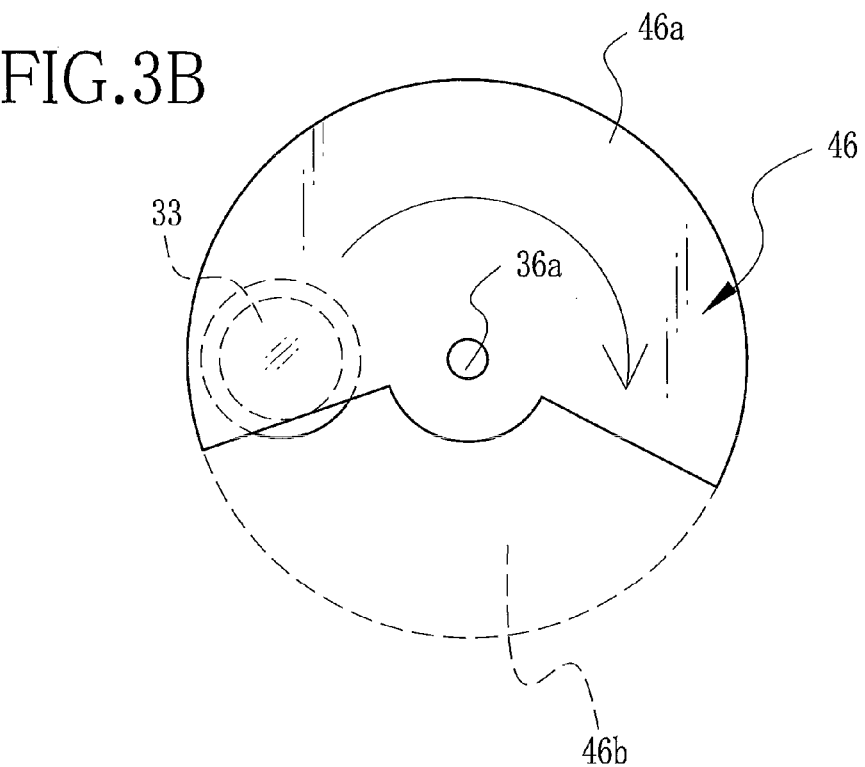

As shown in FIGS. 3A and 3B, the rotating plate 46 of the rotary shutter 35 is a round disk a part of which is cut out in pie shape. The cutout part is a light passing part 46b and the other part is a light blocking part 46a. The rotating plate 46 is connected to a rotation shaft 36a of the motor 36 arranged parallel to an optical axis of the xenon lamp 33. The rotation of the motor 36 alternately enters the light blocking part 46a and the light passing part 46b into an optical path P (see FIG. 2) of the illumination light from the xenon lamp 33. The light passing part 46b enters the optical path P at an illumination period (status shown in FIG. 3A) in which the light is incident on the target body part through the light guide 28, the projection lens 27 and the lighting window 23. The light blocking part 46a enters the optical path P at a light-blocking period (status shown in FIG. 3B). As the motor 36, a pulse motor is used. The motor 36 rotates on a drive pulse supplied from the motor driver 37. Instead of the pulse motor, another motor like DC motor may also be used. The motor driver 37 rotates the motor 36 such that the illumination periods of the rotary shutter 35 are synchronized with the exposure periods of the CCD 20, under the control of the sub CPU 38.

Now the operation of the above configuration will be described with reference to a flow chart shown in FIG. 4. When a medical examination is performed using the electronic endoscope system 2, the connectors 17 and 18 of the electronic endoscope 10 are connected to the processor 11 and the light source device 12, respectively. While the processor 11 and the light source device 12 are being connected, the power switch 13 of the processor 11 is turned on (ST1). Upon turning the power switch 13 on, the main power supply circuit 39 starts to supply the power supply voltage to the lamp power supply circuit 40, the system power supply circuit 41, the motor driver 37, etc. (ST2).

The system power supply circuit 41 supplies the drive power to the main CPU 42, the reset circuit 43, and the sub CPU 38 by transforming the power supply voltage (ST3). When the drive power is normally supplied from the system power supply circuit 41 and the operations of the peripheral circuits become stable, the reset circuit 43 outputs the reset cancel signal to the main CPU 42 and the AND circuit 44 (ST4). When the reset cancel signal is input from the reset circuit 43, the main CPU 42 is activated (ST5).

When the lighting switch 14 is turned on after the main CPU 42 is activated (ST6), the main CPU 42 inputs the lighting instruction signal to the lamp power supply circuit 40 (ST7). Upon receipt of the lighting instruction signal, the lamp power supply circuit 40 firstly applies the trigger voltage to the xenon lamp 33 to start electric discharge. After that, the lamp power supply circuit 40 applies the steady voltage which is lower than the trigger voltage to the xenon lamp 33

(ST8). The application of the trigger voltage, which is relatively high, induces high-frequency noise. Thereafter, when the electric current for illumination is stably applied for longer than a specific period of time by the application of the steady voltage, the lamp power supply circuit 40 outputs the lighting completion signal to the main CPU 42 (ST9). Moreover, the lighting completion signal is input from the main CPU 42 to the AND circuit 44 (ST10). The AND circuit 44 receives the lighting completion signal from the main CPU 42 and the reset cancel signal from the reset circuit 43. As AND of these signals, the AND circuit 44 outputs the reset cancel signal to the sub CPU 38 (ST 11). When the reset cancel signal is input, the sub CPU 38 outputs the drive control signal to the motor driver 37. When the drive control signal is input from the sub CPU 38, the motor driver 37 supplies the drive pulse to the motor 36, and thereby driving and rotating the rotating plate 46 (ST12). Owing to this, the xenon lamp 33 is lit up and the rotary shutter 35 is rotated, and the illumination periods and the light-blocking periods are alternately repeated in synchronization with the exposure periods of the CCD 20. Then, the insert section 15 is inserted into the body cavity, and a user observes the images inside the body cavity captured by the CCD 20 can be viewed on the monitor 32 while inside of the body cavity is illuminated with pulses of the illumination light from the light source device 12.

When the lighting switch 14 of the light source device 12 is turned off after completing the medical examination, the lamp power supply circuit 40 stops applying the steady voltage to the xenon lamp 33 and the motor driver 37 stops supplying the drive pulse to the motor 36. At the same time, the reset signal is output from the reset circuit 43 to the sub CPU 38 through the main CPU 42 and the AND circuit 44. Along with the dropping of the power supply voltage, the supply of the power supply voltage from the main power supply circuit 39 to each component stops, and thus the entire endoscope system 2 is turned off.

As described above, the rotary shutter 35 is actuated after the illumination of the xenon lamp 33 becomes stable. Owing to this, the motor 36 of the rotary shutter 35 is not affected by the high-frequency noise which occurs at the time of applying the trigger voltage to the xenon lamp 33. Therefore, it is prevented that the rotating plate 46 stops in the illumination period due to the loss of synchronization of the motor 36 which may cause the black out of the monitor screen.

According to the above embodiment, although the processor and the light source device are separately provided, the processor and the light source device may be integrated. Moreover, although the electronic endoscope 10 is used as an example, the present invention is applicable to other types of endoscopes, such as an ultrasonic endoscope with an ultrasonic transducer integrated at the distal portion 15a, a fiber scope for observing the condition of an internal body part with the use of optical image guide, and the like.

Various changes and modifications are possible in the present invention and may be understood to be within the present invention.

What is claimed is:

1. A light source device for an endoscope comprising:
   a discharge lamp for emitting illumination light for illuminating inside a human body cavity;
   a lamp controller for controlling emission of said discharge lamp and outputting a lighting completion signal at the time of completing light up of said discharge lamp;
   a rotary shutter opening and closing an optical axis of said illumination light, said rotary shutter alternately providing an illumination period for passing said illumination light and a light-blocking period for blocking said illumination light at a constant period;
   a drive controller for controlling rotation of said rotary shutter; and
   an operation controller for activating said drive controller after said lighting completion signal is output, whereas not activating said drive controller before said lighting completion signal is output.

2. The light source device of claim 1, wherein said rotary shutter has a rotating plate in which a cutout corresponding to said illumination period is formed, and a motor for rotating said rotating plate.

3. The light source device of claim 1, wherein said operation controller including:
   a reset circuit for outputting a reset cancel/reset signal to said lamp controller and said drive controller according to a power on/off; and
   an AND circuit provided between said drive controller and said reset circuit, for obtaining AND of said lighting completion signal and said rest cancel/reset signal;
   and wherein, said operation controller activates said drive controller when both of said reset signal and said lighting completion signal are input to said AND circuit.

4. The light source device of claim 1, wherein said discharge lamp is a xenon lamp.

5. The light source device of claim 1, wherein said lamp controller is a main CPU for taking overall control of said light source device and said drive controller is a sub CPU provided separately from said lamp controller.

* * * * *